US008846358B2

(12) United States Patent
Yoshida et al.

(10) Patent No.: US 8,846,358 B2
(45) Date of Patent: Sep. 30, 2014

(54) METHOD AND DEVICE FOR PRODUCING HYDROGEN

(75) Inventors: Akihito Yoshida, Osaka (JP); Hideaki Yukawa, Kizugawa (JP); Masayuki Inui, Kizugawa (JP)

(73) Assignees: Sharp Kabushiki Kaisha, Osaka (JP); Research Institute of Innovative Technology for the Earth, Kyoto (JP)

( * ) Notice: Subject to any disclaimer, the term of this patent is extended or adjusted under 35 U.S.C. 154(b) by 981 days.

(21) Appl. No.: 12/435,705

(22) Filed: May 5, 2009

(65) Prior Publication Data
US 2009/0280548 A1 Nov. 12, 2009

(30) Foreign Application Priority Data

May 12, 2008 (JP) .................. 2008-124834

(51) Int. Cl.
C12P 3/00 (2006.01)
C12N 9/04 (2006.01)
C12N 1/00 (2006.01)
C12M 1/107 (2006.01)
C12M 1/00 (2006.01)

(52) U.S. Cl.
CPC ........... C12P 3/00 (2013.01); C12Y 101/05006 (2013.01); C12N 9/0006 (2013.01); C12M 21/04 (2013.01); C12M 43/08 (2013.01)
USPC .............. 435/168; 435/190; 435/243

(58) Field of Classification Search
CPC  C12P 3/00; C12Y 101/05006; C12N 9/0006; C12M 21/04; C12M 43/08
USPC .......................... 435/168, 190, 243
See application file for complete search history.

(56) References Cited

U.S. PATENT DOCUMENTS

| | | | |
|---|---|---|---|
| 4,532,210 A | 7/1985 | Miura et al. | |
| 5,834,264 A | 11/1998 | Sanford et al. | |
| 6,395,521 B1 | 5/2002 | Miura | |
| 6,531,239 B2 | 3/2003 | Heller | |
| 6,686,075 B2 | 2/2004 | Gieshoff et al. | |
| 7,432,091 B2* | 10/2008 | Yukawa et al. | 435/168 |
| 2002/0127440 A1 | 9/2002 | Yamamoto et al. | |
| 2006/0128001 A1* | 6/2006 | Yukawa et al. | 435/168 |

FOREIGN PATENT DOCUMENTS

| | | |
|---|---|---|
| JP | 58-60992 | 4/1983 |
| JP | 61-205492 | 9/1986 |
| JP | 4-169178 | 6/1992 |
| JP | 7-218469 | 8/1995 |
| JP | 8-294396 | 11/1996 |
| JP | 10-064572 | 3/1998 |
| JP | 11-016588 | 1/1999 |
| JP | 2000-331702 | 11/2000 |
| JP | 2002-270209 | 9/2002 |
| JP | 2002-270210 | 9/2002 |
| JP | 2003-123821 | 4/2003 |
| JP | 2003-135088 | 5/2003 |
| JP | 2004-303601 A | 10/2004 |
| JP | 2005-87035 A | 4/2005 |
| JP | 2006-055127 | 3/2006 |
| JP | 2006-333767 | 12/2006 |
| JP | 2007-330113 | 12/2007 |

OTHER PUBLICATIONS

Yoshida et al., "Enhanced Hydrogen Production from Formic Acid by Formate Hydrogen Lyase-Overexpressing *Escherida coli* Strains", *Applied and Environmental Microbiology*, vol. 71, No. 11, Nov. 2005, pp. 6762-6768.
Yoshida et al., "Enhanced hydrogen production from glucose using *ldh*- and *frd*-inactivated *Escherida coli* strains", *Appl Microbial Biotechnol.*, vol. 73, 2006, pp. 67-72.
Zinoni et al., Nucleotide sequence and expression of the selenocysteine-containing polypeptide of formate dehydrogenase (formate-hydrogen-lyase-linked) from *Escherida coli*, *Proc. Natl. Acad. Sci.*, vol. 83, Jul. 1986, pp. 4650-4654.
Bohm et al., "Nucelotide sequence and expression of an operon in *Escherida coli* coding for formate hydrogenylase components", *Molecular Microbiology*, vol. 4, No. 2, 1990, pp. 231-243.
International Search Report of PCT/JP2004/002092, mailed May 25, 2004.
Larsson et al., "Kinetics of *Escherichia coli* hydrogen production during short term repeated aerobic-anaerobic fluctuation", *Bioprocess Engineering*, vol. 9, No. 4, 1993, pp. 167-172.
Tanisho et al., "Fermentative hydrogen evolution by *Enterobacter aerogenes* strain E. 82005", International Journal of Hydrogen Energy, vol. 12, issue 9, 1987, pp. 623-627.
Tanisho et al., "Microbial fuel cell using *Enterobacter aerogenes*", Journal of Electroanalytical Chemistry, vol. 275, 1989, pp. 25-32.
Nandi et al., "Involvement of anaerobic reductases in the spontaneous lysis of formate by immobilized cells of *Escherichia coli*", Enzyme and Microbial Technology, vol. 19, pp. 20-25, 1996.
Written Opinion of the International Searching Authority for PCT/JP2004/002092 dated May 6, 2004.
Kayukawa, The Nikkan Kogyo Shinbun, Ltd., Trigger, Jul. 2000, vol. 19, No. 7, pp. 14-16 and 116.
Nikkei Bio-tech, Nikkei Business Publications, Inc., Mikkei Latest Biotechnological Term Dictionary, 4th Edition, p. 346, Jun. 1995.

(Continued)

Primary Examiner — Yong Pak
(74) Attorney, Agent, or Firm — Nixon & Vanderhye P.C.

(57) ABSTRACT

In a step of contacting an organic material including formic acid ions and a carbon source other than the formic acid ions with a microorganism having a formate dehydrogenase gene and a hydrogenase gene under an anaerobic condition, concentration of the formic acid ions in the organic material is set to be not less than 0.01 mol/L and not more than 0.5 mol/L, and concentration of the carbon source is set to not less than 0.1 mmol/L and not more than 200 mmol/L. This allows continuously producing hydrogen for a long time, without dropping the ability of the microorganism to produce hydrogen.

4 Claims, 3 Drawing Sheets

(56) References Cited

OTHER PUBLICATIONS

Palmore et al., "A methanol/dioxygen biofuel cell that uses NAD+-dependent dehydrogenases as catalysts", Journal of Electroanalytical Chemistry, vol. 443, pp. 155-161, 1998.

Suzuki et al, Applied Biochemistry and Bioengineering (1983) vol. 4, pp. 281-310.

Suzuki et al, Biotechnology and Bioengineering Symposium (1978) No. 8, pp. 501-511.

Karube et al, Biotechnology and Bioengineering (1977), vol. 19, No. 11, pp. 1727-1733.

ATCC Bacteria and Bacteriophages, American Type Culture Collection, 1996, Nineteenth Ed., pp. 142-143.

Peck, Jr. et al, "Formic Dehydrogenase and the Hydrogenlyase Enzyme Complex in Coli-Aerogenes Bacteria", J. Bacteriol., 1957, vol. 73, No. 6, pp. 706-721.

Bagramyan et al, The roles of hydrogenases 3 and 4, and the $F_0F_1$-ATPase, in $H_2$ production by *Escherichia coli* at alkaline and acidic pH', FEBS Letters, 2002, vol. 516, pp. 172-178.

\* cited by examiner

F I G. 1
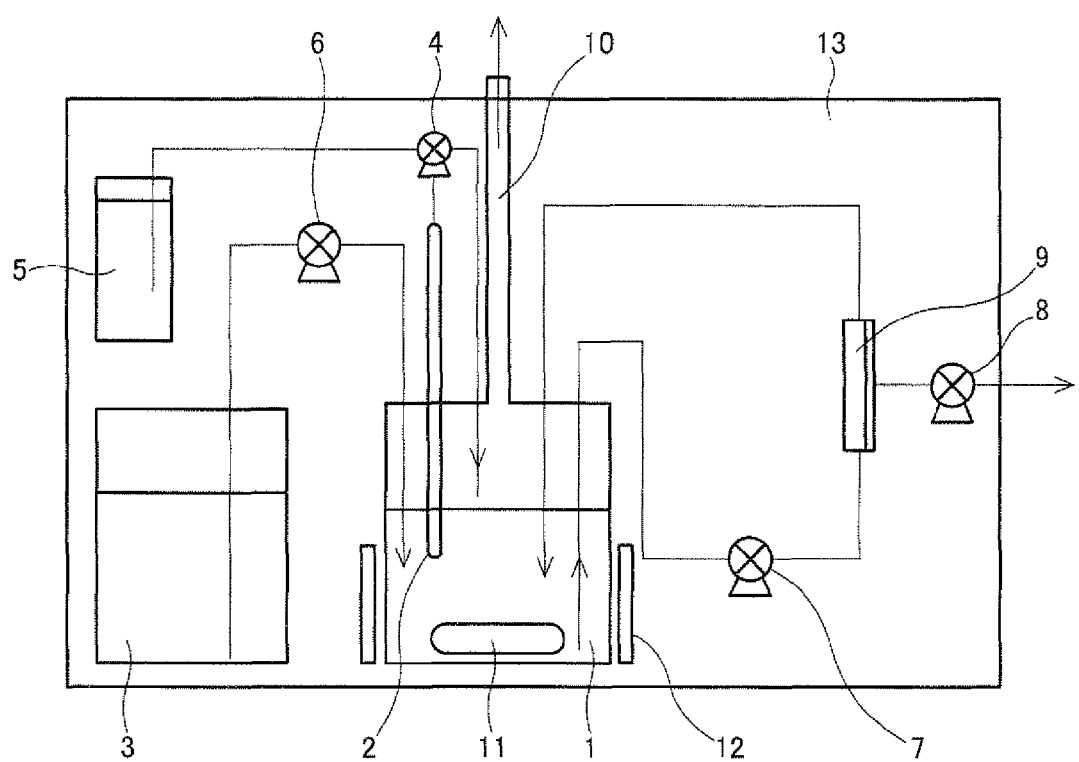

F I G. 2
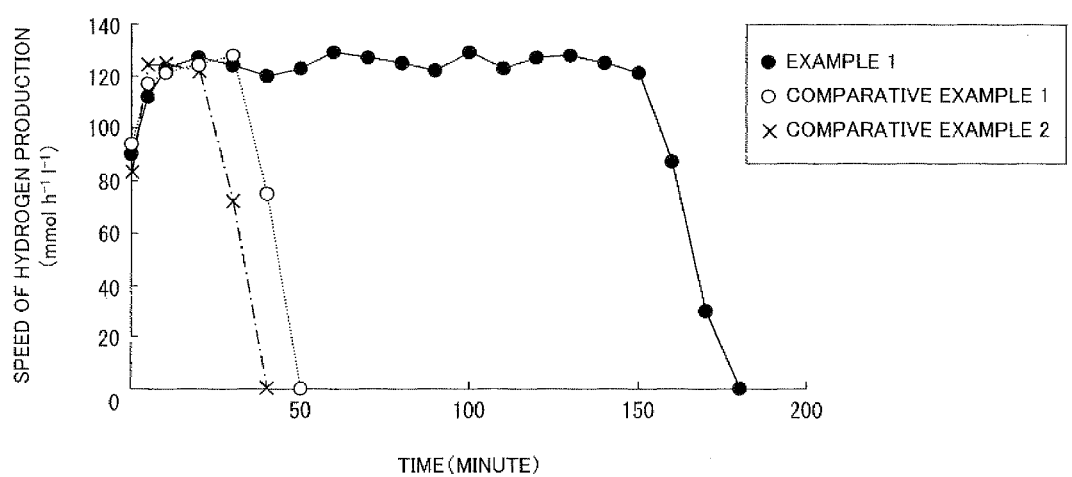

METHOD AND DEVICE FOR PRODUCING HYDROGEN

This Nonprovisional application claims priority under 35 U.S.C. §119(a) on Patent Application No. 2008-124834 filed in Japan on May 12, 2008, the entire contents of which are hereby incorporated by reference.

TECHNICAL FIELD

The present invention relates to a method and device for producing hydrogen, each of which makes use of a microorganism.

BACKGROUND ART

Hydrogen has been spotlighted as an ultimate clean energy source that, when burned, unlike a fossil fuel, does not produce a substance, such as carbon oxide or a sulfur oxide, which may cause an environmental problem. A heat capacity per unit mass of hydrogen is at least three times as much as that of petroleum. Accordingly, if hydrogen is provided to a fuel cell, hydrogen can be converted at a high efficiency to electronic energy or heat energy.

A chemical hydrogen-production method conventionally proposed is a technique such as thermal cracking and steam reforming for natural gas or naphtha. In this method, reaction conditions of a high temperature a high pressure are required. Synthetic gas produced according to this method contains carbon monoxide (CO). Accordingly, in a case where the synthetic gas is used as a fuel for a fuel cell, it is necessary to remove CO for preventing poisoning caused by CO in an electrode catalyst of the fuel cell. However, removal of CO from the synthetic gas is a technically very difficult problem.

As another hydrogen production method, there is a biological hydrogen-production method using a microorganism. The biological hydrogen production method using a microorganism is advantageous in, for example, that reaction conditions of the method are a normal temperature and a normal pressure and that, because produced gas does not contain CO, removal of CO is not necessary. In view of this, the biological hydrogen-production method using a microorganism is spotlighted as a more preferable method for supplying a fuel to a fuel cell.

The biological hydrogen-production method is broadly classified into a method using a photosynthetic microorganism and a method using a non-photosynthetic microorganism (mainly, an anaerobic microorganism). The former method using a photosynthetic microorganism utilizes light energy for hydrogen production. This former method has a low utilization efficiency of light energy and requires a larger area for collecting light. As a result, a hydrogen production device according to the former method has problems to be solved, for example, high cost for a hydrogen production device and difficulty in maintenance. These problems prevent practical implementation of the method using a photosynthetic microorganism.

The latter conventional hydrogen production method using an anaerobic microorganism is a method relying on multiplication of an anaerobic microorganism. In this method, there has been a problem such that a large reaction container is required because a speed of multiplication of the anaerobic microorganism is extremely slow under an anaerobic condition (U.S. Pat. No. 5,834,264 (issued on Nov. 10, 1998)). In view of this problem, a group including an inventor of the present invention has developed a hydrogen production method in which a speed of hydrogen production per unit volume is improved (International Application Publication No. WO2004/074495 A1, pamphlet (published on Sep. 2, 2004)). According to the method described in International Application Publication No. WO2004/074495 A1, pamphlet, when formic acid is used as a material for producing hydrogen, the formic acid added is not retained within a reaction section but immediately decomposed into hydrogen and carbon dioxide.

Another group including the inventor of the present invention discloses that, by culturing a microorganism under control of a concentration of organic acid and/or alcohol in a culture solution under an anaerobic condition, it is possible to cause induced expression of an ability of producing hydrogen in a microorganism that originally does not have the ability of producing hydrogen (Japanese Patent Application Publication, Tokukai, No. 2006-55127 (Publication Date: Mar. 2, 2006)). According to the method described in Japanese Patent Application Publication, Tokukai, No. 2006-55127, a microorganism having an ability of producing hydrogen can be efficiently prepared. In addition, Japanese Patent Application Publication, Tokukai, No. 2006-55127 discloses that: (i) when formic acid is used as a substrate for hydrogen production, a high formic acid concentration is preferable in view of easy control of an amount of liquid of a reaction solution; and (ii) the formic acid concentration is preferably not less than 30% (w/w) and less than 100% (w/w) in an organic material to be supplied.

The another group including the inventor of the present invention has also found that, under control of a formic acid concentration to 250 mmol/L or less in a reaction solution, continuous hydrogen production can be achieved while a cumulative amount of produced hydrogen is not decreased (Japanese Patent Application Publication, Tokukai, No. 2006-333767 (Publication Date: Dec. 14, 2006)). Further, the another group has further found that, for the purpose of preventing a decrease in the cumulative amount of produced hydrogen and continuously producing hydrogen, the formic acid concentration in the organic material to be supplied is controlled more preferably within a range of 0.5 mol/L to 24.0 mol/L while a culture solution is circulated (Japanese Patent Application Publication, Tokukai, No. 2007-330113 (Publication Date: Dec. 27, 2007)).

SUMMARY OF INVENTION

As described above, groups including an inventor of the present invention have proposed hydrogen production methods that do not rely on multiplication of a microorganism with the use of a microorganism having an ability of producing hydrogen. However, formic acid supplied to a reaction solution as an ingredient of a material has an influence on the microorganism and/or a hydrogen-producing enzyme itself. Therefore, the enzyme concerning hydrogen production is denaturalized overtime and the ability of producing hydrogen deteriorates. This makes continuous hydrogen production for a long time impossible.

Further, the formic acid itself hardly serves as a source of nutrition for the microorganism. Accordingly, it has been difficult to maintain and carry on continuous hydrogen production by continuously adding only a high-concentration formic acid. Furthermore, although, under control of the formic acid concentration in the reaction solution, increasing a cumulative amount of produced hydrogen has been attempted (Japanese Patent Application Publication, Tokukai, No. 2006-333767), no consideration is given to an influence of control of a concentration of formic acid to be added and/or a concentration of other substrate on production of hydrogen. In addition, in a case where another source of nutrition is further added when hydrogen is produced continuously for a long time with the use of formic acid as a main material for hydrogen production, the source of nutrition has not effectively served for maintaining the hydrogen production for a long time. This has been a significant problem for actual implementation. These points have been significant problems for carrying out hydrogen production continuously for a long time.

The present invention is attained in view of the above problems. An object of the present invention is to provide a method and a device for producing hydrogen, each of which makes it possible to produce hydrogen steadily for a long time by use of a microorganism.

In order to solve the problem above, inventors of the present invention has diligently studied and found that continuous production of hydrogen by a microorganism with formic acid as a material can be carried out only when (i) a formic acid ion concentration in an organic material supplied to the microorganism is controlled within a predetermined range and (ii) a small amount of a carbon source producing adenosine triphosphate (ATP) is supplied at the time of an anaerobic metabolism. This allowed the inventors to accomplish the present invention.

Conventionally, in a case where a hydrogen production reaction is continuously performed, it is considered to be effective that a concentration of formic acid to be added is set to be high while a concentration of microbial cells is not varied. However, the inventors of the present invention have found that, in a case where a hydrogen production reaction is continuously performed by adding a carbon source in addition to the formic acid, it is significantly important to set a formic acid concentration to be low. Namely, in the present invention, the inventors have found a distinct relation between the formic acid ion concentration and a concentration of a carbon source other than the formic ion. The formic acid ion concentration in the present invention is in a completely different range from a range of a formic ion concentration conventionally disclosed and employed in a continuous hydrogen production reaction.

According to a method for continuously producing hydrogen in accordance with the present invention, even when a hydrogen-producing enzyme is denatured, a carbon source other than the formic acid can steadily cause induced expression of a new hydrogen-producing enzyme. The present invention makes it possible to solve the problems, by controlling the concentrations of the formic acid and the other carbon source that are to be added for newly causing induced expression of the enzyme even in a case where the enzyme is denatured by the formic acid.

That is, the present invention is directed to a method for producing hydrogen from an organic material containing formic acid by use of a microorganism having a formate dehydrogenase gene and a hydrogenase gene, the method including the step of contacting an organic material including formic acid ions and a carbon source other than the formic acid ions with the microorganism under an anaerobic condition, the carbon source serving as a starting material for producing ATP under the anaerobic condition, concentration of the formic acid ions in the organic material being not less than 0.01 mol/L and not more than 0.5 mol/L, and concentration of the carbon source being not less than 0.1 mmol/L and not more than 200 mmol/L. Further, the present invention is directed to a device for producing hydrogen by use of a microorganism having a formate dehydrogenase gene and a hydrogenase gene, the device including: a reaction section for contacting an organic material including formic acid ions and a carbon source other than the formic acid ions with the microorganism under an anaerobic condition; and a material supply section for supplying the organic material, the carbon source serving as a starting material for producing ATP under the anaerobic condition, and the organic material being supplied from the material supply section into the reaction section in such a manner that concentration of the formic acid ions in the organic material is not less than 0.01 mol/L and not more than 0.5 mol/L, and concentration of the carbon source is not less than 0.1 mmol/L and not more than 200 mmol/L.

According to the method and the device for producing hydrogen in accordance with the present invention, a hydrogen-producing enzyme is inducibly expressed in the microorganism during a hydrogen production reaction. Therefore, an ability of producing hydrogen in the microorganism does not deteriorate. Therefore, it is possible to continuously produce hydrogen for a longer time.

For a fuller understanding of the nature and advantages of the invention, reference should be made to the ensuing detailed description taken in conjunction with the accompanying drawings.

BRIEF DESCRIPTION OF DRAWINGS

FIG. 1 is a drawing schematically illustrating a structure of a device for producing hydrogen in accordance with the present invention.

FIG. 2 is a drawing illustrating temporal change in the speed of producing hydrogen in a method for producing hydrogen in accordance with the present invention.

DESCRIPTION OF EMBODIMENTS

[Method for Producing Hydrogen]

Figure 3:
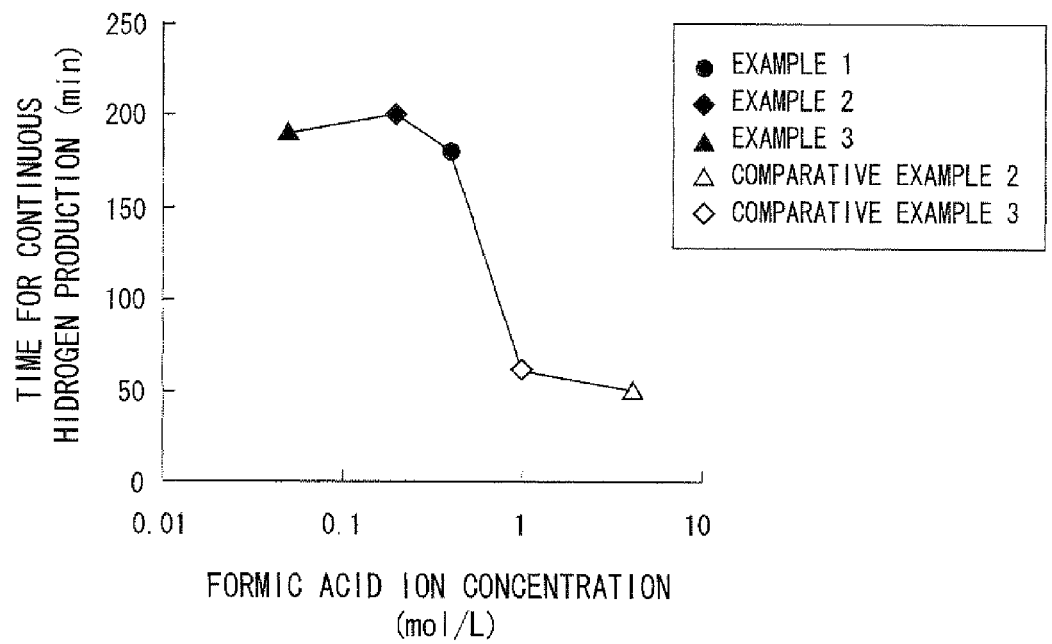
FIG. 3 is a drawing illustrating a time for continuously producing hydrogen in a method for producing hydrogen in accordance with the present invention.

The method for producing hydrogen in accordance with the present invention is a method for producing hydrogen by use of a microorganism having a formate dehydrogenase gene and a hydrogenase gene, the method including the step of contacting an organic material including formic acid ions and a carbon source other than the formic acid ions with the microorganism under an anaerobic condition (hereinafter, simply referred to as a contact step), concentration of the formic acid ions in the organic material being not less than 0.01 mol/L and not more than 0.5 mol/L, and concentration of the carbon source being not less than 0.1 mmol/L and not more than 200 mmol/L.

[Contact Step]

In the present invention, the contact step may be carried out by adding the organic material including the formic acid ion and the carbon source to, for example, a reaction solution including the microorganism. In the method for producing hydrogen using the microorganism in accordance with the present invention, by setting within the range described above the formic acid ion concentration and the carbon source concentration in the organic material to be brought into contact with the microorganism, enzyme activity involved in the hydrogen production is prevented from deteriorating. This makes it possible to produce hydrogen continuously for a long time.

The reaction solution in the specification of the present invention is intended to mean a solution that contains a microorganism used in the hydrogen production reaction occurring in the contact step and that is used in the hydrogen production reaction. Note that the reaction solution during the hydrogen production reaction may contain, for example, the organic material before the reaction and a reaction product produced in the reaction. In the contact step, the organic material is preferably added successively to the reaction solution containing the microorganism. However, if an amount of the organic material present in the reaction system is sufficient for the hydrogen production, the organic material can be added intermittently. A specific state of the contact is not specifically limited as long as the microorganism can come into contact with the organic material. For example, the microorganism and the organic material may be mixed in a conventional and known reaction vessel.

In general, microorganisms are classified into prokaryotes (eubacterium, and archaebacterium) and eucaryotes (alga, protist, fungi, and myxomycete). In the present invention, especially, a prokaryote can be preferably used. In particular, a bacterium among prokaryotes can be preferably used. Moreover, the microorganisms are classified into an aerobic microorganism having a metabolic mechanism based on an enzyme and an anaerobic microorganism having a metabolic mechanism that does not utilize an enzyme. In the present invention, in particular, the anaerobic microorganism can be preferably used.

In such an anaerobic microorganism, various pathways are known as a metabolic pathway in which hydrogen is produced. Examples of such pathways are a pathway in which hydrogen is produced as a metabolic product in a pathway for decomposing glucose to pyruvic acid, a pathway in which hydrogen is produced as a metabolic product in a pathway for converting pyruvic acid to acetic acid via acetyl CoA, a pathway in which hydrogen is produced by having NAD(P)H as a substrate, and a pathway in which hydrogen is produced from formic acid derived from pyruvic acid.

The present invention uses a microorganism having within a cell of the microorganism a metabolic pathway in which hydrogen is produced from formic acid. An example of such a microorganism preferably used is a microorganism having a formate dehydrogenase gene (F. Zioni, et al., Proc. Natl. Acad. Sci. USA, (1986) Vol. 83, p 4650-4654) and a hydrogenase gene (R. Boehm, et al., Molecular Microbiology (1990) Vol. 4, p 231-243).

Specific examples of an anaerobic microorganism having a formate dehydrogenase gene and a hydrogenase gene are: *Escherichia* (such as *Escherichia coli* ATCC 9637, ATCC 11775, ATCC4157, etc.); *Klebsiella* (such as *Klebsiella pneumoniae* ATCC13883, ATCC8044, etc.); *Enterobacter* such as *Enterobacter aerogenes* ATCC13048, ATCC29007, etc.); and *Clostridium* (such as *Clostridium beijerinckii* ATCC25752, ATCC17795 etc.).

The method for producing hydrogen in accordance with the present invention may employ a recombinant microorganism whose ability to produce hydrogen from formic acid is improved. Examples of a method to improve the microorganism's ability to produce hydrogen is a method to cause increased expression of a gene to enforce production of a formate hydrogen lyase (FHL) system in the microorganism, or a method to inactivate in the microorganism an inhibitor gene against production of the FHL system. Here, the "increased expression" means that an amount of expression of a target gene (for example, fhlA gene) is increased. The "increased expression" also includes meaning such that: (i) two or more target genes are included; (ii) the amount of expression is increased by, for example, alteration of a promoter even when only one target gene is included; or the like.

An example of such a recombinant microorganism is a microorganism that has increased expression of a transcription activator gene for the FHL system and that has an inactivated inhibitor gene against production of the FHL system. Microorganisms preferably used in the method for producing hydrogen in accordance with the present invention are, for example, microorganisms produced by a group of inventors of the present invention. Examples of such microorganisms are a microorganism (Accession Number: FERM BP-10444, deposited in International Patent Organism Depositary of National Institute of Advanced Industrial Science and Technology (AIST Tsukuba Central 6, 1-1-1, Higashi, Tsukuba-shi, Ibaraki-ken 305-8566 Japan) on Nov. 9, 2004) that is designated as W3110/fhlA-pMW118 and is a transformant of the *Escherichia coli* (ATC27325), or a microorganism (Accession Number: FERM BP-10443, deposited in International Patent Organism Depositary of National Institute of Advanced Industrial Science and Technology (AIST Tsukuba Central 6, 1-1-1, Higashi, Tsukuba-shi, Ibaraki-ken 305-8566 Japan) on Nov. 9, 2004) that is designated as W3110 ΔhycA/fhlA-pMW118 and is a transformant of the *Escherichia coli* (ATC27325).

It is also possible to use a microorganism obtained by introducing a formate dehydrogenase gene and/or a hydrogenase gene to a microorganism that does not have a formate dehydrogenase gene and/or a hydrogenase gene. A method of introducing the gene to the microorganism is not specifically limited but a known method may be used as the method. Sequences of the formate dehydrogenase gene and the hydrogenase gene can be obtained from, for example, DDBJ/GenBank/EMBL International DNA Database. Examples of the formate dehydrogenase gene are an fdhF gene (Accession number: M13563) derived from *E. coli* and an fdhF gene (Accession Number: X54696) derived from *Enterobacter aerogenes*. Examples of the hydrogenase gene are a hyc gene (Accession Number; X17506) derived from *E. coli*, a hyd gene (Accession Number: X75255) derived from *Pyrococcus furiosus*.

(Concentration of Microbial Cells)

In general, multiplication of a microorganism occurs when a concentration of microbial cells is less than 10% (w/w). (A wet microbial-cell mass is taken as a basis. Hereinafter, the concentration of microbial cells is expressed in the same manner.) Accordingly, for reducing energy used in the multiplication, the concentration of microbial cells is preferably not less than 10% (w/w) in a reaction solution. Meanwhile, when the concentration of microbial cells becomes not less than 80% (w/w), viscosity increases because the microorganisms are filled in at a substantially maximum concentration. Accordingly, in view of diffusion of a substrate and output of hydrogen produced, the concentration of microbial cells in the reaction solution is preferably 80% (w/w) or less. Therefore, in the method for producing hydrogen in accordance with the present invention, the concentration of microbial cells in the reaction solution is preferably set in a range not less than 10% (w/w) and not more than 80% (w/w). The present invention makes it possible to produce hydrogen at a high speed while multiplication of the microorganism does not substantially occur.

Further, in view of an increase in viscosity of the reaction solution including the microorganism, the concentration of microbial cells is preferably not less than 10% (w/w) but not more than 70% (w/w). Further, in view of increasing a hydrogen production amount per unit volume, the concentration of the microbial cells is more preferably not less than 30% (w/w) and not more than 70% (w/w).

(Organic Material)

According to the method for producing hydrogen in accordance with the present invention, the organic material serving as a material for hydrogen production includes a formic acid ion and a carbon source other than the formic acid ion. The organic material may further include nutrition sources explained later.

(Formic Acid Ion)

According to the method for producing hydrogen in accordance with the present invention, the organic material serving as a material for hydrogen production is a solution including a formic acid ion so that gas including hydrogen can be produced through a metabolic pathway via formate dehydrogenase and hydrogenase in a microorganism. In the present invention, formate dehydrogenase and hydrogenase are involved in the production of hydrogen. A formic acid ion concentration in the organic material is preferably not more than 0.5 mol/L. By setting the formic acid ion concentration included in the organic material to not more than 0.5 mol/L, activity of an enzyme (hereinafter, also referred to as a hydrogen-producing enzyme) involved in the hydrogen production can be prevented from deteriorating. The formic acid ion concentration in the organic material is preferably not less than 0.01 mol/L in consideration of easy operation for maintaining the concentration of microbial cells in the reaction solution. Further, right before the organic material is brought into contact with the microorganism, the formic acid ion concentration in the organic material can be diluted into the range described above.

When the formic ion concentration is greater than 0.5 mol/L, it is predicted that the formic acid ion itself may damage ATP synthesis enzyme and the like. Because, for example, ATP itself becomes a precursor for RNA synthesis and ATP is required for aminoacylation of tRNA at the time of translation to proteins, ATP is required in a new synthesis of RNA and proteins. An increase in the formic acid ion concentration is presumed to decrease ATP synthesis and thus decrease the synthesis of the hydrogen-producing enzyme in the microorganism. Therefore, an absolute amount of the hydrogen-producing enzyme can be presumed to decrease as the hydrogen production reaction proceeds.

In preparation of the organic material including the formic acid ion, formic acid or formate is preferably used. Examples of the formate that may be used are: zing formate, sodium formate, potassium formate, caesium formate, nickel formate, barium formate, calcium formate, manganese formate, and ammonium formate. In particular, in view of solubility in water, formic acid, sodium formate, potassium formate, calcium formate, and ammonium formate are preferable. Meanwhile, in view of cost, formic acid, sodium formate, and ammonium formate are more preferable. It is further more preferable to use formic acid because, with the use of formic acid, produced gas only includes hydrogen and carbon dioxide and easily handled. Note that in a case where formate is used, a positive ion of the formate should be separated from a product.

(Carbon Source)

In the hydrogen production reaction according to the present invention, for supplying a microorganism with a nutrition source for causing induced expression of a hydrogen-producing enzyme, an organic material to be brought into contact with the microorganism further includes a carbon source other than the formic acid ion. The "carbon source" is a carbon compound that the microorganism absorbs and utilizes during culturing. The carbon source is preferably a carbon source serving as a starting material in production of ATP by the microorganism under the anaerobic condition. ATP causes the induced expression of the hydrogen-producing enzyme in the microorganism. The "starting material in production of ATP by the microorganism under the anaerobic condition" is intended to mean a material used by the microorganism for producing ATP under the anaerobic condition. Such a starting material may be, for example, a material to be decomposed in metabolic pathways such as a glycolytic pathway and a pentose phosphate pathway, or an intermediate material in these metabolic pathways. Further, "includes a carbon source other than the formic acid ion" is intended to mean that, in addition to formic acid or formate, another carbon source is further included.

In the present specification, the induced expression of the hydrogen-producing enzyme in the microorganism is intended to mean a process in which (i) a factor to induce expression of the hydrogen-producing enzyme and the microorganism are made to coexist and (ii) the enzyme is newly expressed due to the factor and synthesized. For example, in the case of *Escherichia coli*, formic acid is an inducing factor of the hydrogen-producing enzyme. Under the presence of formic acid, induced expression of the hydrogen-producing enzyme is caused within the microorganism by culturing the microorganism by use of a specific nutrition source under an anaerobic condition. To cause induced expressing steadily indicates a state where the inhibitory factor such as organic acid has a little influence on the induction of the hydrogen-producing enzyme, and the induced expression of the enzyme with respect to deactivation of the enzyme is at an equilibrium or rather inclined to express the enzyme.

Such a carbon source is preferably a carbon source of saccharide. The carbon source is more preferably a hydrocarbon compound of saccharide or disaccharide. For example, the carbon source is preferably selected from a group including glucose, xylose, arabinose, fructose, galactose, mannose, lactose, maltose, cellobiose, and sucrose.

Further, in the present invention, when hydrogen is continuously produced, the carbon source is preferably controlled in regard to a speed of supply and added so that the speed of supplying the carbon source into the reaction solution including the microorganism does not become faster than a speed of metabolism of the carbon source by the microorganism. For example, when the carbon source concentration is less than 0.1 mmol/L, induced expression of the hydrogen-producing enzyme is not promoted. When the carbon source concentration is more than 200 mmol/L, the carbon source concentration may result in, due to an osmotic pressure, an inhibitive effect on induced expression of the hydrogen-producing enzyme. Therefore, the carbon source concentration in the reaction solution is preferably controlled in a range of not less than 0.1 mmol/L and not more than 200 mmol/L Here, it is known that, for example, in a case where hexose such as glucose and fructose is used as the starting material, ATP is produced mainly via a glycolytic pathway. It is also known that, for example, in a case where pentose such as xylose and arabinose is used as a starting material, ATP is produced mainly via a pentose phosphate pathway. Further, it is known that, in a case were disaccharide such as sucrose and cellobiose is used as a starting material, first the disaccharide is decomposed into saccharide and then ATP is produced mainly via a glycolytic pathway. The microorganism of the present invention has all the metabolic pathways for metabolizing saccharide. Even when any saccharide is used as the carbon source, it is seen that ATP can be produced. Accordingly, the carbon source used in the present invention is not limited to a specific kind as long as the carbon source can be metabolized in a metabolic pathway of the microorganism in use to produce ATP.

Further, in the present invention, a nitrogen source can also be used as a supplementary nutrition source for synthesis of a hydrogen-producing enzyme. For example, ammonia, ammonium salt, nitrate etc. as an inorganic nitrogen source may be added to an organic material and used. Further, urea, amino acids, protein etc. as an organic nitrogen source may be added to an organic material and used.

Furthermore, for turnover of the hydrogen-producing enzyme, a mineral source may be required. As such a mineral source, for example, potassium hydrogen phosphate and magnesium sulfate each mainly including K, P, Mg, and S may be added to an organic material and used. Other than this, if necessary, it is possible to add to the organic material a minute amount of metal such as Mo, Fe, Se, or Ni and/or a nutrient such as peptone, meat extract, yeast extract, corn steep liquor, casamino acid, and various vitamins such as biotin and thiamin.

In the present invention, gas production is rapid in the liquid solution during the hydrogen production reaction. Accordingly, the reaction solution preferably includes a deformer. A conventionally known deformer can be used as the deformer. Examples of such a deformer are a silicone deformer and a polyether deformer. A method of adding the deformer may be any method such as a method of adding the deformer to the reaction solution in advance, or a method of intermittently or continuously supplying the deformer to the reaction solution.

For keeping the speed of hydrogen production per volume high, the hydrogen production reaction directly from formic acid can be used as a main hydrogen production pathway and other hydrogen production pathway can be used as an auxiliary pathway. As described above, the hydrogen production pathways from other than formic acid are, for example, a pathway in which hydrogen is produced as a metabolic product in a decomposition pathway of glucose to pyruvic acid, a pathway in which hydrogen is produced as a metabolic product in the pathway in which acetic acid is produced via acetyl CoA from pyruvic acid, and a pathway in which hydrogen is produced by using NAD(P)H as a substrate.

(Concentration of Metabolic Product)

Reduction in concentration of a reaction product in the reaction solution results in promoting synthesis of the hydrogen-producing enzyme in the microorganism. In the present specification, the term "reaction product" is used in a manner exchangeable with the term "metabolic product". In the present invention, for reducing the concentration of the metabolic product in the reaction solution, a concentration of the carbon source added to the reaction solution is preferably controlled in a range of not less than 0.1 mmol/L and not more than 50 mmol/L. A method for controlling the concentration of the carbon source to be added may be, for example, a method of detecting the concentration of the carbon source in a culture solution in the reaction solution by a concentration sensor such as a glucose sensor, or a method of detecting the concentration of the carbon source from a rate of change in pH in the reaction solution. Based on the carbon source concentration detected in this way, the carbon source is supplied by an external pump so that an amount of addition of the carbon source becomes optimum.

Examples of the main metabolic products that may be produced in the reaction solution are weak-acid organic acids such as lactic acid, acetic acid, succinic acid, butyric acid, formic acid, pyruvic acid, malic acid, and fumaric acid, and alcohols such as ethanol, butanol, and butanediol. These metabolic products inhibit synthesis of the hydrogen-producing enzyme. In particular, when the concentration of the weak-acid organic acid produced exceeds 100 mmol/L, the organic acid returns back into a cell. Due to the organic acid that has retuned back into the cell, a proton dissociates. This deteriorates a driving force of a proton on an inner side and an outer side of a cell membrane. As a result, ATP synthesis and protein synthesis are inhibited. Therefore, a total concentration of the metabolic products in the reaction solution is preferably controlled in a range of not more than 100 mmol/L. Moreover, for further promoting synthesis of the hydrogen-producing enzyme, the total concentration of the metabolic products in the reaction solution is more preferably controlled in a range of not more than 50 mmol/L.

(Conditions of Hydrogen Production Reaction)

Here, a reaction temperature of the hydrogen production reaction varies depending on types of microorganisms used. However, in general, when a microorganism living at a normal temperature is used, the reaction temperature is preferably in a range of 20° C. to 45° C. The reaction temperature is more preferably in a range of 30° C. to 40° C. in consideration of life duration of the microorganism. Moreover, in the present invention the speed of supplying the organic material may be set as appropriate based on a production speed of hydrogen produced in the reaction. For example, the speed may be set so that 50 mL of the organic material is supplied to the reaction solution per hour.

[Culturing Step of Microorganism]

The method for producing hydrogen in accordance with the present invention may further include a culturing step for culturing the microorganism having the ability to produce hydrogen as described above, before the contact step. If the method for producing hydrogen in accordance with the present invention includes the culturing step, it is preferable to perform preliminary culturing under an aerobic condition and main culturing under an anaerobic condition in the culturing step.

The preliminary culturing under the aerobic condition may be carried out by using a known nutritious culture medium including a nutrition source such as a carbon source, a nitrogen source, and/or an inorganic salt. For the culturing, the culture medium may include one of or a mixture of (i) for example, glucose, fructose, galactose, mannose, lactose, sucrose, cellulose, molasses, and glycerol as the carbon source and (ii) for example, ammonia, ammonium sulfate, ammonium chloride, ammonium nitrate, and urea as the nitrogen source. Further, for example, potassium hydrogen phosphate, potassium dihydrogen phosphate, and magnesium sulfate may be used as the inorganic salt. Other than this, if necessary, it is possible to add as appropriate, to the culture medium, nutrients such as peptone, meat extract, yeast extract, corn steep liquor, casamino acid, and various vitamins such as biotin and thiamin.

The preliminary culturing typically can be carried out at a temperature in a range of approximately 20° C. to 45° C., and preferably in a range of approximately 25° C. to 40° C., under an aerobic condition accompanied by aeration agitation, vibration, or the like. pH in the preliminary culturing is in a range of approximately 5 to 10, preferably in a range of approximately 6 to 8. Adjustment of the pH during the culturing can be carried by addition of acid or alkali. In general, the carbon source concentration at the start of the culturing is preferably in a range of approximately 0.1% (w/v) to 20% (w/v), and more preferably in a range of approximately 1% (w/v) to 5% (w/v). Moreover, a period of culturing may be approximately 0.25 day to 7 days. Such culturing of the microorganism under the aerobic condition may be carried out according to a conventionally known method.

A concentration (w/w %) of the microorganism in the culture solution at the end of the preliminary culturing is preferably 2 times to 1000 times as much as a concentration of the microorganism at the start of the preliminary culturing. In this way, the microorganisms whose number of cells is increased in the preliminary culturing are subjected to main culturing under the anaerobic condition. In the main culturing, it is preferable to separate the microorganism multiplied in the preliminary culturing from a culture solution including a component (such as ethanol, acetic acid, and lactic acid) that inhibits hydrogen production. As a method for such a separation, a general method such as centrifugation or membrane separation can be used.

The concentration of microbial cells in the culture solution under the anaerobic condition is preferably approximately 0.1 mass % to 80 mass % for obtaining microorganisms that express an ability to produce hydrogen. The concentration is more preferably approximately 1 mass % to 80 mass % for efficiently obtaining microorganisms having the ability to produce hydrogen.

The anaerobic condition can be confirmed by a redox potential in the culture solution being in a range of approximately −100 mV to −500 mV and more preferably in a range of approximately −200 mV to −500 mV. An example of a method for adjusting an anaerobic state of the culture medium is a method of removing dissolved gas by heating, reducing pressure, or bubbling of nitrogen gas for example. An example of a method for removing the dissolved gas, particularly, dissolved oxygen in the culture solution is a method of degassing under a reduced pressure of not more than approximately $13.33 \times 10^2$ Pa, preferably not more than approximately $6.67 \times 10^2$ Pa, or further preferably not more than approximately $4.00 \times 10^2$ Pa for approximately 1 minute to 60 minutes or preferably approximately 5 minutes to 60 minutes. Further, a reducing agent may be added to the solution if necessary. Examples of the reducing agent used are thioglycolic acid, ascorbic acid, cysteine hydrochloride, mercapto acetic acid, thiol acetic acid, glutathione, and sodium sulfate. One type of or a combination of two or more types of these reducing agents may be used.

The culturing of the microorganism under the anaerobic condition may be performed by using a known culture medium including, for example, a carbon source, a nitrogen source, and/or a mineral source. The carbon source and the nitrogen source used in the culture solution of the microorganism under the anaerobic condition may be the same as the carbon source and the nitrogen source used in the culture solution of the microorganism under the aerobic condition. Moreover, examples of the mineral source that can be used are: potassium hydrogen phosphate, magnesium sulfate, potassium sulfate, sodium chloride, iron sulfate, zinc sulfate, copper sulfate, manganese sulfate, calcium chloride, and sodium tetraborate, each including Na, K, P, or S for example. Other than this, if necessary, it is possible to add to the culture medium an antibiotic such as ampicillin sodium or kanamycin, or a nutrient such as peptone, meat extract, yeast extract, corn steep liquor, casamino acid, and various vitamins such as biotin and thiamin.

Further, the culture medium may contain a minute amount of a metal component. Though a necessary minute amount of a metal component varies depending on types of microorganisms, examples of such metal components are: iron, molybdenum, selenium, and nickel. Examples of compounds containing these metals are: sodium molybdate anhydrous, sodium selenite pentahydrate, hexaammonium heptamolybdnate, nickel ammonium sulfate, and sodium selenite. Note that a considerable amount of these metal components are contained in a natural nutrition source such as yeast extract, it is dispensable to add a minute amount of these metal components.

As conditions for culturing under the anaerobic condition, a temperature range is approximately 20° C. to 45° C., and preferably approximately 25° C. to 40° C. A pH range is approximately pH 4.0 to pH 10.0, and preferably approximately pH 5.0 to pH 8.0. In general, a carbon source concentration at the start of culturing is in a range of preferably approximately 0.1% (W/V) to 20% (W/V), and more preferably in a range of approximately 1% (W/V) to 5% (W/V).

In this way, by use of the microorganism obtained in a culturing step including the preliminary culturing and the main culturing, or by use of the culture solution containing the microorganism, the contact step described above may be carried out. Note that the main culturing in the culturing step and the contact step can be performed in the same anaerobic condition.

[Step of Separating Metabolic Product]

The method for producing hydrogen in accordance with the present invention may further include a step of separating from the reaction solution a metabolic product resulting from hydrogen production reaction. The step of separating the metabolic product from the reaction solution may be carried out by separating microorganisms in the reaction solution from a liquid component in the reaction solution. Examples of a method for separating microorganisms from the liquid component in the reaction solution include sedimentation separation, centrifugal separation, filtration separation etc. In particular, the filtration separation is preferable since it allows high-speed and continuous separation.

In order to control concentration of the metabolic product in the reaction solution, it is possible to detect concentration of components in the reaction solution by use of a concentration sensor such as an alcohol sensor in a case where the metabolic product is alcohol such as ethanol, and by use of a rate of change of pH etc. in the reaction solution in a case where the metabolic product is an organic acid. The microorganisms in the reaction solution are separated from the liquid component according to the detected concentration of the metabolic product, and the liquid component is replaced with a liquid that does not include a metabolic product such as an organic acid. This allows controlling the concentration of the metabolic product in the reaction solution.

The method for separation by use of the filtration separation is a method for separation by use of a porous film and a pressure difference. Examples of the method include dead-end filtration separation and cross-flow filtration separation. In the cross-flow separation, a supernatant component in the reaction solution flows in a tangential direction and the surface of a film is constantly washed. This allows keeping stable filtration speed regardless of proceeding of filtration.

Therefore, in the present invention, it is preferable to use the cross-flow filtration separation. Providing an additional function such as inverse washing allows recovering filtration performance when filtration performance drops due to accumulation of microorganisms etc. on the surface of the film in the course of separation. Examples of a structure of a film used in the cross-flow filtration separation include a flat film cassette, a hollow fiber, a tubular film etc. In particular, it is preferable to use the flat film cassette and the hollow fiber in view of a ratio of film area with respect to volume.

Examples of a material for the film used in the cross-flow filtration separation include a macromolecule film such as regenerated cellulose, polyamide, polyfluorovinylidene, and polyethersulfone, and a ceramic film such as alumina. The diameter of a pore of the film for separating microorganisms from the liquid component in the reaction solution is preferably in a range of 0.01 to 5 µm, and more preferably in a range of 0.01 to 2 µm.

In the case of using a filter section for the cross-flow filtration separation, the liquid component containing nutrition, metabolic products etc. is removed from a reaction section. It is necessary to keep the amount of the liquid in the reaction section within a predetermined range from the amount that has been originally set. The predetermined range is preferably within ± (plus minus) 20% of the amount of the reaction solution. The amount of the liquid being not more than − (minus) 20% of the amount of the reaction solution is not preferable since microbial cell concentration in the reaction solution increases and viscosity of the liquid solution increases. Further, the amount of the liquid being not less than + (plus) 20% is not preferable since a dead space in the reaction section is reduced, yielding an adverse effect on extraction of produced gas from the reaction solution.

[Step of Recovering Hydrogen]

The method for producing hydrogen in accordance with the present invention may further include a step of separating hydrogen from the produced gas and recovering hydrogen. The step of separating hydrogen from the produced gas may include analyzing components in the produced gas by use of a gas chromatography etc., and separating gas containing much hydrogen by a general method such as a film separation method and an adsorption method. In the method for producing hydrogen in accordance with the present invention, gas mainly including hydrogen and carbon dioxide is produced. Therefore, the gas containing much hydrogen may be separated from the produced gas.

As described above, with the method for producing hydrogen in accordance with the present invention, it is possible to prevent activity of a hydrogen-producing enzyme in the hydrogen producing reaction from dropping, and to greatly lengthen a time for continuously producing hydrogen (a time from start of hydrogen producing reaction to stop of the reaction). In the present invention, it is possible to reduce the adverse influence of formic acid having high concentration supplied as a material component on a microorganism's performance for producing hydrogen. In the hydrogen producing reaction using an organic material containing formic acid, a hydrogen-producing enzyme is denatured by formic acid and activity of the hydrogen-producing enzyme drops. In the present invention, in order to supplement induction expression of the hydrogen-producing enzyme, a carbon source other than formic acid ions is further added, thereby controlling concentration of the carbon source to be added.

[Hydrogen Producing Device]

The present invention also provides a device for producing hydrogen. The device for producing hydrogen in accordance with the present invention is a device for producing hydrogen by use of a microorganism having a formate dehydrogenase gene and a hydrogenase gene, including a reaction section for contacting (i) an organic material containing formic ions and a carbon source other than formic ions with (ii) the microorganism, concentration of the formic acid ions contained in the organic material supplied into the reaction section being not less than 0.01 mol/L and not more than 0.5 mol/L, and concentration of the carbon source being not less than 0.1 mmol/L and not more than 200 mmol/L.

The device for producing hydrogen in accordance with one embodiment of the present invention is explained below with reference to FIG. 1. As illustrated in FIG. 1, the device for producing hydrogen in accordance with the present invention includes a reaction section 1, a pH sensor 2, a material tank 3, a pH controller 4, a pH adjusting solution supply section 5, a supply pump (material supply section) 6, a circulating pump 7, a liquid component discharge pump 8, a filter section 9, a gas extraction section 10, a stirring section 11, a temperature control section 12, and a control box 13.

The reaction section 1 is provided with the stirring section 11 and the temperature control section 12. Into the reaction section 1 is poured a reaction solution containing a microorganism having a formate dehydrogenase gene and a hydrogenase gene. When an organic material containing formic acid is supplied from the material tank 3 into the reaction section 1, the hydrogen-producing enzyme in the reaction solution containing the microorganism causes a reaction of producing hydrogen. The produced hydrogen is extracted outside by the gas extraction section 10.

The reaction solution in the reaction section 1 is circulated in such a manner that the reaction solution is discharged by the circulating pump 7, caused to pass the filter section 9, and returned to the reaction section 1. In this process, the liquid component in the reaction solution is separated by the filter section 9, and the liquid component is discharged outside by the liquid component discharge pump 8. The liquid component is a liquid containing nutrition such as a carbon source, a nitrogen source, and inorganic salts, and a solute such as a metabolic product of a microorganism and an unreacted organic material. That is, the liquid component indicates a component that is other than the microorganism in the reaction solution.

Since the formic acid in the organic material supplied to the reaction section 1 is instantly separated into hydrogen and carbon dioxide in the reaction section 1, concentration of the forming acid in the discharge solution is low. Therefore, the speed of discharge of the liquid component by the liquid component discharge pump 8 may be set to be lower than the speed of supplying the material by the supply pump 6, in accordance with the amount of formic acid dissolved in the reaction section 1. Since the liquid component is separated from the reaction solution when the reaction solution passes through the filter section 9, microbial cell concentration in the reaction solution gets higher. Thus, the reaction solution is circulated and the liquid component is partially discharged during the circulation, so that liquid level in the reaction section 1 is kept constant.

The filter section 9 may be provided outside the reaction section 1 or may be provided inside the reaction section 1. That is, the filter section 9 may be provided outside or inside the reaction section 1 as long as the liquid component in the reaction solution can be discharged from the reaction section 1. Formic acid having high concentration that is a material of hydrogen in the discharged liquid component may be diluted and then reused.

There is a case where the reaction solution contains nutrition such as a carbon source, a nitrogen source, and inorganic salts and a solute such as a metabolic product. In this case, the liquid component in the reaction solution which is discharged by the filter section 9 contains the nutrition and the metabolic product. In particular, it is necessary to keep concentration of the nutrition constant by supplying, into the reaction solution, nutrition whose amount corresponds to that of the discharged nutrition. The liquid level in the reaction solution 1 can be controlled also by supplying necessary nutrition etc. from the supply tank 3, or by providing another supply orifice and supplying nutrition etc. via the supply orifice.

It is desirable that pH of the hydrogen producing reaction ranges from 4.5 to 8.0. When pH of the reaction solution in the reaction section 1 greatly exceeds the range in the process of the reaction, a pH adjusting solution is supplied if necessary from the pH adjusting solution supply section 5 into the reaction section 1, so as to control pH. The pH sensor 2 detects pH of the reaction solution in the reaction section 1, and the pH controller 4 controls supply of the pH adjusting solution from the pH adjusting solution supply section 5.

For example, when pH of the reaction solution gets too acidic, a basic aqueous solution such as a sodium hydroxide solution, a potassium hydroxide solution, and ammonium aqueous solution may be used as the pH adjusting solution. When pH of the reaction solution gets too basic, an acidic aqueous solution such as hydrochloric acid and sulfuric acid may be used as the pH adjusting solution. In FIG. 1, only one pH controller 4 and only one pH adjusting solution supply section 5 are provided. Alternatively, in a case where pH of the reaction solution gets both acidic and basic, the pH controllers 4 may be provided for supplying an acidic adjusting solution and a basic adjusting solution, respectively, and the pH adjusting solution supply sections 5 may be provided for supplying an acidic adjusting solution and a basic adjusting solution, respectively.

The organic material filled in the material tank 3 is supplied via the supply pump 6 to the reaction section 1. In order to promote synthesis of the hydrogen-producing enzyme in the reaction section 1, it is preferable that concentration of the carbon source and concentration of the metabolic product in the reaction solution can be detected. Speed of the supply pump 6 supplying the organic material is controlled according to the detected concentrations. If concentration of the formic acid ions to be added to the reaction section 1 is high, there is a case where a microorganism or the hydrogen-producing enzyme in the microorganism is partially damaged. In order to prevent this, there may be provided a system for diluting an organic material right before the organic material is supplied to the reaction section 1. In FIG. 1, only one material tank 3 is provided. Alternatively, the material tank may be divided into two or more tanks such as a formic acid tank and a carbon source tank. In this case, the amounts of the formic acid and the carbon source may be controlled by detecting respective concentrations thereof in the reaction section 1 and feeding back the results of the detections to supply pumps 6 provided for the formic acid and the carbon source, respectively.

In the present embodiment, components in the device for producing hydrogen are sealed in the control box 13. Since the method for producing hydrogen in accordance with the present invention is carried out under an anaerobic condition, anaerobic atmosphere is kept in the reaction section 1. For example, the atmosphere in the reaction section 1 may be inert gas such as nitrogen gas, which is not essential since spinner culture under the anaerobic condition involves production of gas. The reaction solution must be used in a reduced state. The anaerobic condition for the reaction solution is such that redox potential preferably ranges from −100 mV to −500 mV and more preferably ranges from 20 mV to −500 m. For example, in a case where oxygen is temporarily mixed into the reaction solution, when microbial cell concentration in the reaction solution is high, the mixed oxygen is instantly consumed and an anaerobic state is kept again. Therefore, mixture of oxygen is allowed as long as the mixture does not deteriorate activity of the hydrogen-producing enzyme.

In the present embodiment, it is preferable that a hydrogen sensor is placed on the reaction section 1 or the gas extraction section 10. Further, it is preferable that a detector for detecting produced gas, such as a flow meter, is placed on the reaction section 1 or the gas extraction section 10. This allows monitoring the speed of production of gas. Gas extracted from the gas extraction section 10 may be separated by a gas separation device (not shown) etc. into gas containing much hydrogen. The gas separator separates the gas containing much hydrogen from gas mainly containing hydrogen and carbon dioxide which is produced in the reaction section 1. The method for separating the gas may be a general method such as a film separation method and an adsorption method.

The device for producing hydrogen by use of a microorganism in accordance with the present invention generates gas mainly including hydrogen and carbon dioxide, and does not basically generate carbon monoxide (CO). In general, in a case where hydrogen is used as a fuel for a solid macromolecule fuel cell as of this date, it is necessary to keep CO in the cell not more than 10 ppm by use of a system for removing carbon monoxide (CO transformer, CO remover etc.) since CO is produced due to hydrogen production reaction. On the other hand, a fuel cell employing the present invention does not generate CO due to hydrogen production reaction. The fuel cell employing the present invention is preferable in this regard since the fuel cell does not require a system for removing CO, allowing a simpler configuration. Further, in general, a conventional reforming method using natural gas requires reforming temperature not less than 600° C., which requires a reaction device capable of dealing with a high temperature. On the other hand, a temperature at the reaction in the present invention is substantially a room temperature, which does not require such a special reaction device.

[Fuel Cell]

The present invention further provides a fuel cell including the aforementioned device for producing hydrogen. The fuel cell allows generation of electricity by use of hydrogen gas supplied to a fuel electrode from the device for producing hydrogen in accordance with the present invention and by use of oxygen in the air supplied to an air electrode. Since the fuel cell includes the device for producing hydrogen in accordance with the present invention, hydrogen serving as a fuel is continuously supplied to the fuel cell for a long time. This allows the fuel cell to generate electricity for a long time.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

The following specifically explains Examples of the present invention. Note that the present invention is not limited to the following Examples.

Example 1

Production of hydrogen was repeated by use of recombinant *Escherichia coli* (deposit number: FERM BP-10443, W3110 ΔhycA/fhlA-PMW118, National Institute of Advanced Industrial Science and Technology, International Patent Organism Depositary (AIST Tsukuba Central 6, 1-1-1, Higashi, Tsukuba-shi, Ibaraki-ken 305-8566 Japan) on Nov. 9, 2004)).

Ampicillin sodium (manufactured by Wako Pure Chemical Industries, Ltd.) and glucose (manufactured by Wako Pure Chemical Industries, Ltd.) were added to a culture solution (BC culture medium) having a composition in Table 1, in such a manner that the content of ampicillin sodium was 50 mg/L and the content of glucose was 5.0 g/L. In a flask containing 100 mL of the culture solution, the recombinant *Escherichia coli* was subjected to a shaking culture (preliminary culturing) under an aerobic condition at 37° C. for one night. Table 1 shows the composition of the BC culture medium containing ampicillin sodium. The reagents in Table 1 and added formic acid were products of Wako Pure Chemical Industries, Ltd.

TABLE 1

| Composition | Amount |
| --- | --- |
| Water | 1000 ml |
| Diammonium hydrogen phosphate | 10 g |
| Potassium sulfate | 2.0 g |
| Sodium chloride | 0.3 g |
| Magnesium sulfate | 0.2 g |
| Iron sulfate | 4.0 mg |
| Zinc sulfate | 0.9 mg |
| Copper sulfate | 0.4 mg |
| Manganese sulfate | 0.2 mg |
| Calcium chloride | 0.8 mg |
| Sodium tetraborate | 0.09 mg |
| Hexammonium heptamolybdnate | 0.4 mg |
| Nickel ammonium sulfate | 0.9 mg |
| Sodium selenite | 0.6 mg |

Then, 100 mL of the culture solution having been subjected to the preliminary culturing was put in 10 L of the BC culture medium in Table 1 that contained 50 mg/L of ampicillin sodium and 5.0 g/L of glucose, and was subjected to anaerobic culture (main culturing) at 37° C. for 24 hours. 5.0 mol/L of a sodium hydroxide aqueous solution (manufactured by Wako Pure Chemical Industries, Ltd.) was added when needed so that pH of the culture solution was kept at 6.0 in the anaerobic culture. Then, the culture solution was subjected to a centrifuge (5000 rpm, 15 minutes) so as to remove supernatant, and thus a microorganism capable of producing hydrogen was obtained. The microorganism thus obtained was suspended in a culture solution in Table 1 that did not contain glucose, and a reaction solution was prepared so that the amount thereof was 200 mL. Herein, microbial cell concentration was approximately 20% (w/w).

The following explains a method for producing hydrogen with reference to FIG. 1 schematically illustrating the device used in this Example. First, a reaction solution containing a microorganism whose microbial cell concentration was 20% (w/w) was supplied to the reaction section 1. Further, a BC culture medium in Table 1 that contained 0.4 mol/L of formic acid and 30 mmol/L of glucose was prepared and poured into the material tank 3. The filter section 9 was provided with a pencil-type module microza (manufactured by Asahi Kasei Corporation). The liquid component discharge pump & was adjusted and set so that the amount of a liquid in the reaction section 1 could be kept at the amount that had been initially set. The stirring section 11 for rotating the reaction solution so as to promote mixture of the reaction solution was provided in the reaction section 1. Further, the control box 13 was sealed so as to maintain anaerobic atmosphere in the control box 13.

The supply pump 6 was controlled so that the material was continuously supplied to the reaction section 1 at feeding speed of 50 mL/h, and the amount of produced gas and the speed of gas production were measured. The speed of gas production was measured by use of a mass flowmeter (MODEL3810, manufactured by KOFLOC). At the same time as supply of the material, the circulating pump 7 and the liquid component discharge pump 8 were operated and circulation and filtration of the reaction solution was started. Gas production occurred at the same time as supply of the material. Analysis of collected gas by use of a gas chromatography (GC14B, manufactured by Shimadzu Corporation) showed that the produced gas contained approximately 50% of hydrogen and remaining percentage of carbon oxide gas etc.

Right after the material was supplied to the reaction section 1, the speed of hydrogen production got stable, and a constant speed of producing 120 mmol of hydrogen per 1 L of the reaction solution was kept for one hour. Thereafter, a rapid drop of the speed of hydrogen production was observed when a time of continuously producing hydrogen (time from start of hydrogen producing reaction to end of the reaction) exceeded approximately 160 hours. The result of the present Example shows that the method for producing hydrogen in accordance with the present invention allowed stable and continuous production of hydrogen for approximately one week. It is considered that in the method for producing hydrogen in accordance with the present invention, although activity of a hydrogen-producing enzyme drops due to formic acid, a hydrogen-producing enzyme is induced and expressed by glucose, allowing continuous production of hydrogen for a long time.

Further, a part of the reaction solution was discharged outside while continuously producing hydrogen, and concentration of a metabolic product in the reaction solution was measured after 50, 100, and 150 hours has passed. Each of the reaction solutions measured after 50, 100, and 150 hours from the start of the reaction contained 5 mmol/L of lactic acid, 15 mmol/L of acetic acid, 5 mmol/L of succinic acid, and 10 mmol/L of ethanol as metabolic products. The concentrations of individual metabolic products did not vary with respect to the time from the start of the reaction, and could be controlled to be constant. The total concentration of the metabolic products in each sample did not exceed 100 mmol/L.

In the present Example, the reaction was made with microbial cell concentration being approximately 20%. The same stable and continuous reaction was observed for approximately one week, when the microbial cell concentration was approximately 40% or 60%.

Examples 2 and 3

In order to analyze the influence of concentration of formic acid ions when continuously producing hydrogen, the concentration of formic acid ions was changed as follows in the BC culture of FIG. 1 that was a material to be poured into the material tank 3.

Example 2. BC culture with concentration of formic acid ions being 0.2 mol/L

Example 3: BC culture with concentration of formic acid ions being 0.05 mol/L

Examples 2 and 3 were made under the same conditions as those for Example 1, except that the above BC cultures were used and the liquid component discharge pump 8 was adjusted so as to supply the material in order that the speed of supplying the material is the same as the speed of producing hydrogen. Here, concentration of glucose in the material was fixed to 30 mmol/L.

Right after the material was supplied into the reaction section 1, a constant speed of producing approximately 120 mmol of hydrogen per 1 L of the reaction solution was kept for one hour. A time for continuously producing hydrogen was approximately 200 hours (Example 2) or approximately 190 hours (Example 3). As described above, in Examples 2 and 3, too, it is possible to stably and continuously generate hydrogen for approximately one week.

Examples 4 and 5

In order to analyze the influence of concentration of glucose during the reaction of continuously producing hydrogen, the concentration of glucose was changed as follows in the BC culture of FIG. 1 that was a material to be poured into the material tank 3.

Example 4: BC culture with concentration of glucose being 10 mmol/L

Example 5: BC culture with concentration of glucose being 150 mmol/L

Examples 4 and 5 were made under the same conditions as those for Example 1, except that the above BC cultures were used. Here, concentration of formic acid ions in the material was fixed to 0.4 mol/L.

Right after the material was supplied into the reaction section 1, a constant speed of producing approximately 120 mmol of hydrogen per 1 L of the reaction solution was kept for one hour. A time for continuously producing hydrogen was approximately 160 hours (Example 4) or approximately 150 hours (Example 5). As described above, in Examples 4 and 5, too, it is possible to stably and continuously generate hydrogen for approximately one week.

Further, a part of the reaction solution was discharged outside while continuously producing hydrogen in Example 5, and concentration of a metabolic product in the reaction solution was measured after 50, 100, and 150 hours from the start of the reaction. Each of the reaction solutions measured after 50, 100, and 150 hours from the start of the reaction contained approximately 10 mmol/L of lactic acid, approximately 25 mmol/L of acetic acid, approximately 10 mmol/L of succinic acid, and approximately 20 mmol/L of ethanol as metabolic products. The concentrations of individual metabolic products did not vary with respect to the time from the start of the reaction, and could be controlled to be constant. The total concentration of the metabolic products in each sample did not exceed 100 mmol/L.

Comparative Examples 1-4

As Comparative Examples of the method for producing hydrogen in accordance with the present invention, the BC cultures in Table 1 whose concentration of formic acid ions and whose concentration of glucose were adjusted as follows were poured into the material tank 3.

Comparative Example 1: BC culture with concentration of formic acid ions being 0.4 mol/L Comparative Example 2: BC culture with concentration of formic acid ions being 4 mol/L and concentration of glucose being 30 mmol/L Comparative Example 3: BC culture with concentration of formic acid ions being 1 mol/L and concentration of glucose being 30 mmol/L Comparative Example 4: BC culture with concentration of formic acid ions being 0.4 mol/L and concentration of glucose being 210 mmol/

Comparative Examples 1-4 were made under the same conditions as those for Example 1, except that the above BC cultures were used and the liquid component discharge pump 8 was adjusted so as to supply the material in order that the speed of supplying the material is the same as the speed of producing hydrogen.

Right after the material was supplied into the reaction section 1, a constant speed of producing 120 mmol of hydrogen per 1 L of the reaction solution was kept for one hour. However, thereafter, the speed of producing hydrogen greatly dropped approximately 40 hours later in Comparative Example 1 in which the material did not contain glucose; approximately 30 hours later in Comparative Example 2; approximately 50 hours later in Comparative Example 3; and approximately 40 hours later in Comparative Example 4.

FIG. 2 illustrates a graph showing temporal change in continuous production of hydrogen under the conditions for Example 1 and Comparative Examples 1 and 2, respectively. As illustrated in FIG. 2, appropriately controlling concentration of formic acid ions and concentration of glucose in the material poured into the reaction section 1 allows greatly lengthening the time for continuously producing hydrogen.

Further, FIG. 3 illustrates a graph in which a time for continuously producing hydrogen is plotted while concentration of glucose in the material was fixed to 30 mmol/L and concentration of formic acid ion was changed. As illustrated in FIG. 3, in a case where concentration of formic acid ions in the material is less than 0.01 mol/L, in order to keep the amount of the material solution in the reaction section 1 constant, it is difficult to filtrate the microorganism and to discharge the material solution due to performance and operativity of a filter, making it impossible to carry out continuous hydrogen production. From this fact, it was found that fixing concentration of glucose in the material remarkably lengths the time for continuously producing hydrogen with concentration of formic acid ions being not less than 0.01 mol/L and not more than 0.5 mol/L.

Figure 4:
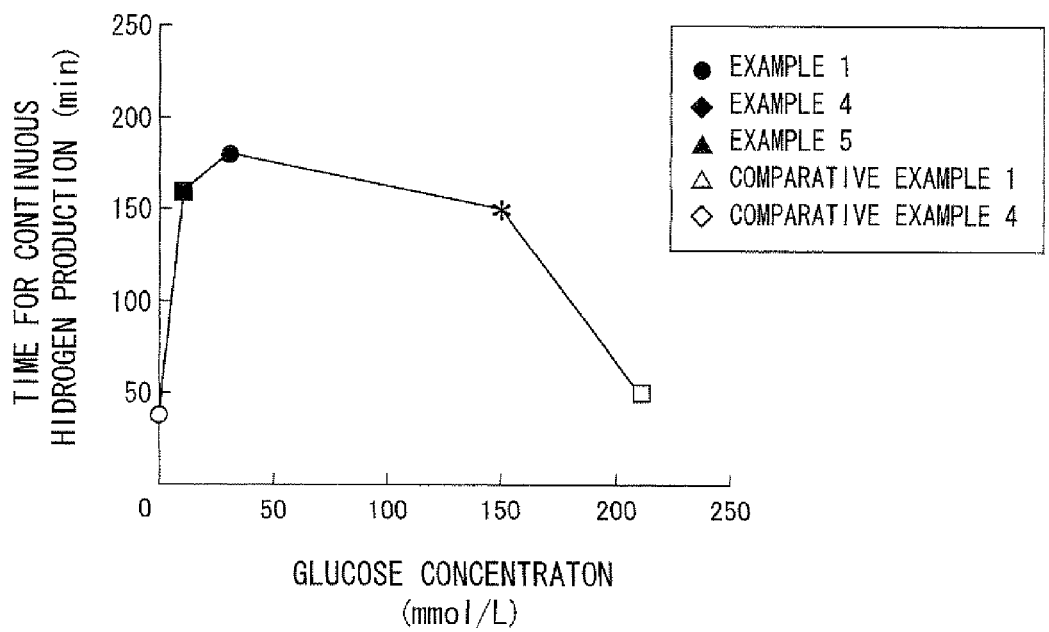
FIG. 4 is a drawing illustrating a time for continuously producing hydrogen in a method for producing hydrogen in accordance with the present invention.

Further, FIG. 4 illustrates a graph in which the time for continuously producing hydrogen (time from start of hydrogen producing reaction to end of the reaction) is plotted while concentration of formic acid ions in the material was fixed to 0.4 mol/L and concentration of glucose was changed. As illustrated in FIG. 4, adding a small amount of glucose in the material remarkably lengthens the time for continuously producing hydrogen. Further, when the concentration of glucose exceeds 200 mmol/L, the effect of adding glucose is lost. Therefore, it was found that when the concentration of formic acid ions in the material to be supplied is fixed to 0.4 mol/L, setting the concentration of glucose to be not less than 0.1 mmol/L and not more than 200 mmol allows remarkably lengthening the time of continuously producing hydrogen.

Comparative Example 5

In Comparative Example 5, hydrogen was continuously produced under the same conditions as those for Example 1 by use of the device illustrated in FIG. 1. In Comparative Example 5, there was reused a metabolic product solution to which formic acid and glucose were added so that when the metabolic product solution was discharged by the liquid component discharge pump 8, concentration of formic acid ions was 0.4 mol/L and concentration of glucose was 30 mmol/L in the metabolic product solution. The metabolic product solution was poured as a material into the material tank 3, and the continuous hydrogen production reaction was started. The reaction solution after 0.5 hour from the start of the reaction contained approximately 20 mmol/L of lactic acid, approximately 50 mmol/L of acetic acid, approximately 20 mmol/L of succinic acid, and approximately 40 mmol/L of ethanol as metabolic products (the total concentration of the metabolic products in the reaction solution was 130 mmol/L).

As described above, in Comparative Example 5, it was found that the reaction solution contained more than 100 mmol/L of the metabolic products. Further, as a result of the continuous hydrogen production reaction, it was found that the total concentration of all the metabolic products gradually increased as the time for continuous reaction elapsed. Further, after 40 hours from the start of the reaction, rapid drop of the speed of producing hydrogen was observed. Consequently, it was found that when concentration of the metabolic product that derives from a carbon source and that generates ATP in an anaerobic metabolic process is controlled to be not more than 100 mmol/L, the time for continuously producing hydrogen is remarkably lengthened.

As described above, the present invention provides a method and a device for producing hydrogen each capable of continuously producing hydrogen for a long time, by controlling ion concentration of formic acid to be added as a material to a microorganism and concentration of a carbon source other than the formic acid ions.

The method for producing hydrogen in accordance with the present invention allows continuously producing hydrogen for a long time. Therefore, applying the method to a fuel cell etc. allows continuously generating electricity for a long time. Accordingly, the present invention is widely applicable to the field of manufacturing electronic devices and the field of generating energy.

It is preferable to arrange the method for producing hydrogen in accordance with the present invention so that the carbon source serves as a starting material for producing ATP under the anaerobic condition. Further, it is preferable to arrange the method so that the carbon source is a hydrocarbon compound consisting of monosaccharide or disaccharide. Further, it is preferable to arrange the method so that the carbon source is selected from the group consisting of glucose, xylose, arabinose, fructose, galactose, mannose, lactose, sucrose, maltose, and cellobiose. Consequently, ATP that serves as a power to cause induced expression of a hydrogen-producing enzyme is effectively supplied.

It is preferable to arrange the method so that concentration of a metabolic product in a reaction solution containing the microorganism is not more than 100 mmol/L. Consequently, ATP produced by the microorganism can be effectively used for production of the hydrogen-producing enzyme.

It is preferable to arrange the method so that microbial cell concentration of the microorganism in the reaction solution containing the microorganism is not less than 10 mass percent and not more than 80 mass percent. This allows reducing energy used for multiplication of the microorganism. Further, since increase in viscosity due to close filling of the microorganism can be prevent, it is possible to effectively diffuse a substrate, to effectively discharge produced hydrogen etc.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

The invention claimed is:

1. A method for producing hydrogen by use of a microorganism having a formate dehydrogenase gene and a hydrogenase gene, the method comprising the step of contacting an organic material including formate and a carbon source other than the formate with the microorganism under an anaerobic condition, the carbon source serving as a starting material for producing ATP under the anaerobic condition, concentration of the formate in the organic material being not less than 0.01 mol/L and not more than 0.5 mol/L, and concentration of the carbon source being not less than 0.1 mmol/L and not more than 200 mmol/L, wherein the concentration of a weak-acid organic acids and alcohols in a reaction solution containing the microorganism is controlled in a range of not more than 100 mmol/L.

2. The method as set forth in claim 1, wherein the carbon source is a hydrocarbon compound consisting of monosaccharide or disaccharide.

3. The method as set forth in claim 1, wherein the carbon source is selected from the group consisting of glucose, xylose, arabinose, fructose, galactose, mannose, lactose, sucrose, maltose, and cellobiose.

4. The method as set forth in claim 1, wherein microbial cell concentration of the microorganism in the reaction solution containing the microorganism is not less than 10 mass percent and not more than 80 mass percent.

* * * * *